United States Patent
Grawe et al.

(12)

(10) Patent No.: US 6,290,931 B1
(45) Date of Patent: Sep. 18, 2001

(54) HOMOGENEOUS PREFORMULATIONS CONTAINING HIGH CONCENTRATIONS OF STEROIDS, FOR PRODUCING LOW-DOSE SOLID AND SEMI-SOLID PHARMACEUTICAL PREPARATIONS

(75) Inventors: Detlef Grawe, Kleinromstedt; Peter Hoesel; Peter Moellmann, both of Jena; Carsten Timpe, Weissenborn; Michael Dittgen, Apolda; Klaus Matthey, Jena, all of (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/319,802

(22) PCT Filed: Dec. 15, 1997

(86) PCT No.: PCT/DE97/02915

§ 371 Date: Jun. 10, 1999

§ 102(e) Date: Jun. 10, 1999

(87) PCT Pub. No.: WO98/26762

PCT Pub. Date: Jun. 25, 1998

(30) Foreign Application Priority Data

Dec. 16, 1996 (DE) ............................... 196 52 196

(51) Int. Cl.[7] ...................................... A61K 9/12
(52) U.S. Cl. ............... 424/45; 424/46; 424/43; 424/489
(58) Field of Search ................... 424/40, 43, 45, 424/489

(56) References Cited

FOREIGN PATENT DOCUMENTS 0 503 521 A1   9/1992   (EP) .

OTHER PUBLICATIONS

M. Dittgen et al, 'Zur Pharmazeutischen Technologie Der Granulierung', Pharmazie 35, H. 4, pp. 237–249, 1980.*
E. Nuernberg, 'Darstellung Und Eigenschaften Pharmazeutisch Relevanter Spruehtrocknungstechnologie', Acta Pharmaceutica technologica, 26(1), pp. 40–47, 1980.*
H. Kala, 'The Use of Spray Drying in Pharmacy', Pharmazie, 34, H. 12, pp. 779–784, 1979.*
J Broadhead, et al: "The Spray Drying of Pharmaceuticals", Drug Development and Industrial Pharmacy, 18 (11&12), pp. 1169–1206, 1992.
J. Cooper und J.S. Rees: "Tableting Research and Technology", J. Pharm. Sci. 61 (1972), pp. 1551–1555.

* cited by examiner

Primary Examiner—Raj Bawa
(74) Attorney, Agent, or Firm—Michael J. Striker

(57) ABSTRACT

A homogeneous steroid-containing preformulation for production of solid and semi-solid pharmaceutical preparations containing a uniform constant dosage of at least one steroid in a range from 0.001 to 1 percent by weight is described. This steroid-containing preformulation contains of from 0.001 to 50 percent by weight of the at least one steroid. The homogeneous steroid-containing preformulation is made by a method including dissolving the at least one steroid in a solvent to form a dispersant; dispersing an adjuvant consisting of adjuvant particles in the dispersant in a mass ratio of the adjuvant to the at least one steroid of 1:1 to 1000:1 to form a suspension; and creating a spray-mist of the suspension so as to evaporate and remove the solvent from the suspension and thus to form a dried particulate which includes steroid-containing particles. The droplets in the spray mist have a droplet diameter greater than a mean diameter of the adjuvant particles. The maximum particle size of the dried particulate forming the steroid-containing preformulation is increased by less than 30 percent in comparison to an average particle size of the adjuvant particles.

6 Claims, No Drawings

HOMOGENEOUS PREFORMULATIONS CONTAINING HIGH CONCENTRATIONS OF STEROIDS, FOR PRODUCING LOW-DOSE SOLID AND SEMI-SOLID PHARMACEUTICAL PREPARATIONS

This application is a 371 of PCT/DE97/02915 filed Dec. 15, 1997

BACKGROUND OF THE INVENTION

1. Field of the Invention

The invention relates to homogeneous preformulations containing high concentration of steroids, for producing low-dose solid and semi-solid pharmaceutical preparations having a concentration content of 0.001 to 1 weight percent of steroid.

2. Prior Art

The invention also relates to a method for producing the homogeneous preformulations, containing steroids in high concentration, for the claimed low-dose solid and semi-solid pharmaceutical preparation.

It is known that the homogeneous distribution of active ingredients is an essential prerequisite for the reliable effect of a medication.

The problem of homogeneous active ingredient distribution arises especially in single-dose solid and semi-solid forms of preparation in which the active ingredient is not in dissolved form, such as in tablets, lozenges, capsules and suppositories.

The prerequisite for the homogeneous distribution of active ingredients in the single-dose forms of medication is on the one hand a uniform distribution of the active ingredient in the basic mixture or preformulation and on the other the preservation of this distribution during further processing. Nonhomogeneities in the mixture of active ingredients and adjuvants and inaccuracies in further processing are added together and lead to fluctuations in dosage in solid and semi-solid single dose forms of medication.

In high-dose preparations, as a rule no serious mixing nonhomogeneities occur.

In low-dose forms of medication, the primary problem is to furnish a sufficiently homogeneous distribution, which is stable against demixing, of the very low mass of active ingredient in proportion to the mass of the pharmaceutical adjuvants.

From the professional and patent literature, low-dose solid and semi-solid preparations containing steroids are known; the preformulations are produced by means of dry and moist granulation technologies or dry mixing processes.

M. Dittgen, H. Kala et. al., for instance, in "Zur pharmazeutischen Technologie der Granulierung" [On the pharmaceutical technology of granulation], Pharmazie 35, 4, pages 237 to 249, 1980, describe such granulation technologies.

It is problematic by means of the mixing process to achieve good content uniformity while avoiding demixing and sizing effects, for instance from defluidizing and outgassing of fine active ingredient particles from the fluidized bed.

Formulations produced by these technologies have the disadvantages of the use of micronized active ingredients and the attendant necessity of one additional process step;

derived from this the possibility of recrystallization and clumping by way of the active surfaces of the active ingredient particles and the attendant negative effects on homogeneity and release properties.

In a special form of the fluidized bed-spray granulation process, the use of micronized active ingredients is circumvented by dissolving the active ingredient in an organic solvent at high dilution and spraying it onto a large-particle adjuvant moving in a fluidized bed and granulating it by building on that structure.

The disadvantages of the formulations produced by this method are:

the occurrence of deviations from the desired steroid content by outgassing of fine steroidal abrasion from the fluidized bed;

the fact that because of the long dwell times in the production process, undesired decomposition processes can occur in thermally unstable active ingredients.

One disadvantage of the method that should not be underestimated is that large quantities of solvent are in the final steps of the galenic preparation, which requires major effort and expense for equipment and safety technology (explosion proofing together with rendering nitrogen inert).

In European patent disclosure EP 0 503 521, it is described that a direct-tabletable pharmaceutical preparation is attained by dry mixing of micronized steroids with certain excipients (spray-dried lactose).

This proves to have the following disadvantages:

Only selected excipients have the requisite adsorptive properties;

The loading capacity of the surfaces is only very limited;

once again, micronized active ingredients are used, which have the disadvantage of recrystallization and clumping along the active surfaces of the active ingredient particles and the attendant negative effects on homogeneity and release properties.

M. Dekker, in "The spray drying of pharmaceuticals", Drug Development and Industrial Pharmacy", 18 (11 & 12) pages 1169 through 1206, 1992, and E. Nürnberg, in "Darstellung und Eigenschaften pharmazeutisch relevanter Sprühtrocknungsprodukte" [Characterization and properties of pharmaceutically relevant spray drying products], Acta Pharmazeutica Technologica, 26(1), pages 40 to 67, 1980 describe the use of spray drying technology for the galenic formulation of pharmaceutical active ingredients, including steroids.

With the spray drying, primarily retardant effects or effects that improve solubility and stability are attained by way of active ingredient imbedding or microencapsulations (for instance in polymeric adjuvants) or inclusion complexes (in cyclodextrins).

According to J. Cooper and J. E. Rees, "Tableting research and technology" J. Pharm. Sci. 61 (1972) pages 1551 to 1555, the spray drying can be used for coating medication particles with protective casings and for modifying the physical properties of the active ingredients and adjuvants, with the goal of making their further processing (such as tablets) easier.

According to H. Kala et.al., "The use of spray drying in pharmacy", Pharmazie, 34, No. 12 (1979) pages 779 to 784, the use of spray drying for attaining certain properties in active ingredients and adjuvants that go beyond simple drying and simultaneous micronization is fundamentally known.

For example, metastable medication modifications or amorphous active ingredients can be produced in standardized fashion, in order to improve the speed of dissolution or to preclude uncertainty factors dictated by the existence of various crystal modifications.

In this connection, spray imbedding in various adjuvants and spray drying of suspensions of a solution of medication and insoluble adjuvant (celluloses) are mentioned in particular.

H. Kala et.al. also mention that spray products (adjuvants as dry binders, active ingredients, and combinations) in the form of spherical, free-flowing particles have already been used for direct tableting.

M. Dekker, in "The spray drying of pharmaceuticals", Drug Development and Industrial Pharmacy, 18 (11 & 12) pages 1169 through 1206, 1992, mentions that fine, free-flowing adjuvant granulates (fillers, binders, explosives, pigments) for direct tableting can be produced by spray drying.

The goal of this spray granulation process is to attain more favorable processing properties, which however as a rule are associated with an increased particle size, for direct tableting.

The disadvantage of these technologies with a view to direct production of low-dose pharmaceutical preparations is as follows:

because of the large particle size of these granulates, the requisite content uniformity does not always exist through subsequent mixing;

the spray granulation of the necessarily highly dilute steroid solutions or suspensions is very complicated and expensive, because of the large volumes involved.

SUMMARY OF THE INVENTION

Homogeneous preformulations containing high concentration of steroids, for producing low-dose solid and semi-solid pharmaceutical preparations having a concentration content of 0.001 to 1 weight percent of steroids and the production of a homogeneous preformulation, containing steroids in high concentration, for low-dose solid and semi-solid pharmaceutical preparation with a concentration content of 0.001 to one weight percent of steroid by means of spray drying, in which in a conventional dry mixing process while avoiding the above disadvantages the preformulation can be processed into a direct-tabletable pharmaceutical preparation, are not described in the patent and professional literature.

The object of the invention is to furnish steroid-containing preformulations that assure the production of low-dose solid and semi-solid pharmaceutical preparations with a concentration content of 0.001 to 1 weight percent of steroid with good homogeneity of the steroid adjuvant, along with good stability of the active ingredient distribution in the pharmaceutical preparation. This object is attained according to the invention by furnishing homogeneous preformulations containing high concentration of steroids, for producing low-dose solid and semi-solid pharmaceutical preparations having a concentration content of 0.001 to 1 weight percent of steroid, obtained by evaporation of the dispersant, containing the steroidal active ingredient, from a suspension with dispersed pharmaceutically conventional adjuvant, in which a spray mist is created, whose mean droplet diameter is greater than the mean diameter of the adjuvant particles, and the maximum particle size of the dried particles of the steroid containing preformulation is increased by less than 30 percent in comparison to the particle size of the adjuvant.

It proves to be especially advantageous if the maximum particle size of the dried particles of the dried particles of the steroid-containing preformulation is increased by less than 10% in comparison with the particle size of the adjuvant.

It is also especially advantageous that the concentration of the steroidal active ingredient in the steroid-containing preformulation amounts to from 5 to 30 weight percent.

According to the invention the method of making the homogeneous steroid-containing preformulation comprises the steps of:

a) dissolving steroid or steroid ingredients in a solvent to form a dispersant;

b) dispersing an adjuvant consisting of adjuvant particles in the dispersant in a mass ratio of adjuvant to the steroid or steroid ingredients of 1:1 to 1000:1 to form a suspension; and c) creating a spray-mist of the suspension so as to evaporate and remove the solvent from the suspension and thus to form a dried particulate comprising a plurality of steroid-containing particles, the spray mist comprising a plurality of droplets having a droplet diameter greater than a mean diameter of the adjuvant particles; wherein a maximum particle size of the dried particulate comprising the steroid-containing preformulation is increased by less than 30 percent in comparison to an average particle size of the adjuvant particles.

DETAILED DESCRIPTION OF THE PREFERRED EMBODIMENTS

As the sexual hormone, one component from the group comprising estrogens, gestagens and antigestagens, or a component that quickly splits off the above active ingredients after administration, is preferably used.

The method of the invention for producing the homogeneous preformulations containing steroids in high concentration will now be described in further detail:

The steroidal active ingredient or active ingredients are dissolved in a suitable solvent, such as ethanol.

Stability-improving adjuvants that speed up resorption or modify the release kinetics are optionally added. Next, the adjuvant is suspended with a mass ratio to the dissolved steroid of 1:1 to 100,000:1. A range of from 2:1 to 20:1 proves to be especially advantageous for the method. As adjuvants, alpha-lactose monohydrate, microcrystalline cellulose or inorganic calcium salts, preferably in micronized form, can be used.

Next, the suspension is spray-dried for the sake of gentle, rapid removal of the solvent and stable and finely dispersed distribution of the active ingredient on the surface of the adjuvant.

It is especially notable that from the sprayed suspension, active ingredient particles and adjuvant particles are not dried side by side. By a selection of the process conditions in the spraying process, the active ingredient can be bonded virtually completely and materially to the adjuvant.

An essential role is played by the particle size distribution of the active ingredient, the solid concentration of the suspension, the active ingredient concentration of the solution, and the droplet size distribution in the spray mist, which in turn is substantially affected by the effect of the atomizer device (nozzle or disk) and by the viscosity of the solution.

The spray process should be conducted such that the mean droplet diameter in the spray mist is greater than the mean diameter of the adjuvant particles, but on the other hand is not so great that a substantial increase in particle size occurs from granulation.

The process conditions should be adjusted specifically to suit the spray drying equipment used and the system of substances involved.

The steroidal preformulations thus produced are mixed dry in a suitable mixture together with other direct-tabletable adjuvants, such as Tablettose, Ludipres, Emcompress, or Avicel, and then filled into hard gelatin capsules or in the form of an oily suspension in soft gelatin capsules, or tableted in the usual way. The tablets are made into lozenges or coated in aqueous or organic fashion, together with the usual, known adjuvants.

With the invention, homogeneous preformulations containing high concentration of steroids, for producing low-dose solid and semi-solid pharmaceutical preparations having a concentration content of 0.001 to 1 weight percent of steroid are furnished, which are distinguished by their homogeneity and stability to demixing, and the steroidal active ingredient is contained in finely dispersed form, materially bonded to the adjuvant.

Surprisingly, it has been found that steroidal preformulations of this kind can be processed in a suitable mixture in dry fashion along with the usual tableting adjuvants without problems to produce low-dose pharmaceutical preparations with very good, stable active ingredient homogeneity.

Testing for uniformity of the content of the single-dose forms of medication is done as prescribed by PhEur and DAB 9.

Testing is based on the determination of the medication content of a number of single-dose units in order to ascertain whether the single content is within the defined limits, referred to the average content of a model specimen.

Execution:

In ten units extracted arbitrarily by the random sample process, the medication content is determined individually, with the aid of a suitable analytic method.

Table 1 shows the properties of tablets whose preformulation was produced by exemplary embodiment 2.

Tablets Containing 30 µg of Ethinyl Estradiol

| Content uniformity according to Ph. Eur./DAB: | 29 µg |
|---|---|
| Relative standard deviation (S rel): | 2.26% |

The homogeneity is proved in accordance with the Content Uniformity Test—to be employed with a proportion of active ingredient of 50 mg and less per individual dose.

The following was also demonstrated:

| Release of active ingredient (n = 6) | 82% after 45 min |
|---|---|
| Requirement: | >=75% after 45 min |
| S rel: | 1.53% |
| Hardness (n = 10): | 35.6 N |
| Uniformity of the tablet composition per Ph. Eur./DAB: | attained |
| Mean tablet mass (n = 100): | 50.7 mg |
| S rel: | 2.10% |
| Max: | 54.0 mg |
| Min: | 49.0 mg |

Table 2 shows the properties of tablets whose preformulation is produced in accordance with exemplary embodiment 3.

Tablets Containing 250 µg of Sulfamate Steroid

| Content uniformity according to Ph. Eur./DAB: | 253 µg |
|---|---|
| Relative standard deviation (S rel): | 1.28% |

The homogeneity is proved in accordance with the Content uniformity test—to be employed with a proportion of active ingredient of 50 mg and less per individual dose.

The following was also demonstrated:

| Release of active ingredient (n = 6) | 101.0% after 45 min |
|---|---|
| Requirement: | >=75% after 45 min |
| S. rel: | 3.4% |
| Decomposition time: | 1:19 min |
| Hardness (n = 10): | 36.7 N |
| Uniformity of the tablet composition per Ph. Eur./DAB: | attained |
| Mean tablet mass (n = 100): | 51.9 mg |
| S rel: | 0.86% |
| Max: | 53.0 mg |
| Min: | 51.0 mg |

Table 1 and Table 2 show that the steroidal preformulations of the invention can be processed to make low-dose pharmaceutical preparations with very good, stable active ingredient homogeneity.

The advantages of the method of the invention for producing the homogeneous preformulations of the invention that contain steroids in high concentration are:

Very good, stable active ingredient homogeneity in the pharmaceutical preparation for tableting.

The limit particle size of the preformulation, which is important for subsequent mixing processes, is defined by the choice of the adjuvant particle size, since this particle size is increased only insignificantly (see Examples 1–3 and Tables 3–5) by the spraying on of the active ingredient.

Nonhomogeneities and demixing or sizing effects during the subsequent mixing process are thus avoided.

The advantageous galenic properties of the adjuvant are transferred to the preformulation, and the solid properties of the active ingredient are stabilized.

Clumping and attendant changes in activity, as are often observed in micronized steroids, did not occur.

The use of micronized steroids can be dispensed with. This means that one complicated process step can be eliminated. Micronized steroid active ingredients, such as desogestrel, often have a tendency to later recrystallization and clumping effects, which are deleterious to the active ingredient homogeneity and release.

At the same time, the influence of crystallization in producing the active ingredient, or in other words the often complicated definition and validation of the crystal structure and crystallinity, is averaged out.

The preformulations are stable to demixing and can be stored.

By the spray drying of the suspension droplets (adjuvant particles sheathed with active ingredient solution), which are finely distributed in a drying gas, via a nozzle or atomizer disk, a material and finely dispersed bonding of the active ingredient with the adjuvant surface is attained by a rapid evaporation of the solvent. As a result the adsorptive properties of the adjuvant, which in the prior art are decisive for dry mixing with micronized steroids and which substantially restrict the selection of adjuvants, are of only secondary importance.

The loading of the adjuvant with active ingredients can be substantially greater than in mechanical mixing of the adjuvant with micronized steroids.

A loading ratio of 1 (gram of steroid to gram of adjuvant) can be attained.

The attainable loading is dependent only on the solubility of the steroid in the solvent used, on the droplet size (spray conditions), and on the particle size of the adjuvant.

In common with the dissolved steroid and suspended adjuvant, other adjuvants that improve stability, speed up resorption or modify the release kinetics and that can be present in dissolved or suspended form can be spray dried.

Incorporating these adjuvants already in the preformulation stage makes the mixing stage of the pharmaceutical final formulation easier extends the above-discussed advantages of spray drying with regard to the steroid distribution on the adjuvant to these adjuvants as well.

It is also possible, for instance by using suitable soluble adjuvants, to embed the active ingredient in molecularly dispersed form in the adjuvant sheath and thus to speed up or slow down the release or to protect the active ingredient against the environment.

By way of the spray process, more galenic possibilities are thus opened up than by way of dry mixing of micronized steroids and adjuvants.

The spray drying process, since the evaporation of the solvent takes place within fractions of a second, is an extremely gentle process precisely for thermally vulnerable steroids (such as sulfamate steroids).

The above-discussed advantages allow the flexible production of steroidal preformulations with specific galenic properties as for the pharmaceutical final formulation of the tablet composition.

The galenic complication and the pharmaceutical technology for the final formulation are drastically reduced and simplified.

The preformulations produced in a preliminary step, heavily loaded with steroid and thus low in quantity, can be processed without problems by the dry mixing process to produce very homogeneous tablets with the usual tableting adjuvants.

The production of the preformulations of the invention will be described in further detail in the ensuing examples, but is not limited by them.

EXAMPLE 1

25 g of desogestrel are dissolved in 562 g of ethanol (96%, DAB) and 63 g of water.

To the clear solution, 125 g of lactose monohydrate (Sorbolac 400, Meggle) are added while stirring.

The suspension is dried with a dryer with a dual-substance nozzle in the parallel-flow process.

Conditions:

| | |
|---|---|
| Air inlet temperature: | 115° C. |
| Air outlet temperature: | 66° C. |
| Inflow of the suspension: | 10 ml/min |
| Spray pressure (N2): | 2.5 bar (ü) |
| Nozzle: | 0.7 mm |
| Drying air: | 350 L/min |

The dry product is precipitated using a cyclone.

Particle Size Analysis:

| | Lactose used $\mu m$ | Preformulation $\mu m$ |
|---|---|---|
| ×10 | 1.57 | 3.37 |
| ×50 | 7.94 | 10.76 |
| ×90 | 24.18 | 26.75 |

The figures given are statements pertaining to the maximum particle size. For instance, ×90 states that 90% of the lactose used and of the preformulation are smaller in their particle size than 24.18 and 26.75 $\mu m$, respectively.

EXAMPLE 2

12 g of ethinyl estradiol are dissolved in 180 g of ethanol (96%, DAB).

To the clear solution, 48 g of lactose monohydrate (Sorbolac 400, Meggle) are added while stirring.

The suspension is dried with a dryer with a dual-substance nozzle in the parallel-flow process.

| | |
|---|---|
| Air inlet temperature: | 140° C. |
| Air outlet temperature: | 74° C. |
| Inflow of the suspension: | 10 ml/min |
| Spray pressure (N2): | 1.3 bar (ü) |
| Nozzle: | 0.7 mm |
| Drying air: | 300 L/min |

The dry product is precipitated using a cyclone.

Particle Size Analysis:

| | Lactose used $\mu m$ | Preformulation $\mu m$ |
|---|---|---|
| ×10 | 1.34 | 1.69 |
| ×50 | 6.10 | 7.05 |
| ×90 | 18.02 | 20.36 |

EXAMPLE 3

6 g of a sulfamate steroid are dissolved in 240 g of ethanol (96%, DAB).

To the clear solution, 22 g of lactose monohydrate (Sorbolac 400, Meggle) are added while stirring.

The suspension is dried with a dryer with a dual-substance nozzle in the parallel-flow process.

| | |
|---|---|
| Air inlet temperature: | 120° C. |
| Air outlet temperature: | 62° C. |
| Inflow of the suspension: | 10 ml/min |
| Spray pressure (N2): | 1.3 bar (ü) |
| Nozzle: | 0.7 mm |
| Drying air: | 300 L/min |

The dry product is precipitated using a cyclone.
Particle Size Analysis:

| | Lactose used μm | Preformulation μm |
|---|---|---|
| ×10 | 1.34 | 1.43 |
| ×50 | 6.10 | 6.40 |
| ×90 | 18.02 | 19.86 |

The particle size analyses show that by the choice of the adjuvant particle size, the limit particle size of the preformulation which is important for subsequent mixing processes is defined, since this particle size is increased only insignificantly by the spraying on of the active ingredient. Nonhomogeneities and demixing and sizing effects during the subsequent mixing process are thus avoided.

What is claimed is:

1. A method of producing a homogeneous steroid-containing preformulation containing at least one steroid in a concentration of from 0.001 to 50 percent by weight, said preformulation comprising a starting material for production of solid and semi-solid pharmaceutical preparations containing a uniform constant dosage of said at least one steroid, said dosage of said at least one steroid being in a range from 0.001 to 1 percent by weight, said method comprising the steps of:

a) dissolving the at least one steroid in a solvent to form a dispersant;

b) dispersing an adjuvant consisting of adjuvant particles in said dispersant in a mass ratio of the adjuvant to the at least one steroid of 1:1 to 1000:1 to form a suspension; and c) creating a spray-mist of the suspension so as to evaporate and remove said solvent from said suspension and thus form a dried particulate comprising a plurality of steroid-containing particles, said spray mist comprising a plurality of droplets having a droplet diameter greater than a mean diameter of said adjuvant particles;

wherein a maximum particle size of the dried particulate comprising the steroid-containing preformulation is increased by less than 30 percent in comparison to an average particle size of said adjuvant particles.

2. The method as defined in claim 1, wherein said mass ratio of said adjuvant to said at least one steroid is from 2:1 to 20:1.

3. The method as defined in claim 1, wherein said maximum particle size of said dried particulate is increased by less than 10% in comparison to said average particle size of said adjuvant particles.

4. The method as defined in claim 1, wherein said steroid-containing preformulation includes from 5 to 30 percent by weight of said at least one steroid.

5. The method as defined in claim 1, wherein said adjuvant is selected from the group consisting of alpha-lactose monohydrate, microcrystalline cellulose and inorganic calcium salts.

6. The method as defined in claim 1, wherein said solvent is ethanol or a mixture of ethanol and water.

* * * * *